United States Patent
Chu et al.

(10) Patent No.: US 7,726,971 B2
(45) Date of Patent: Jun. 1, 2010

(54) COLORED DENTAL POST

(75) Inventors: Manh-Quynh Chu, Fontanil Cornillon (FR); Pierre-Luc Reynaud, Vaulnaveys le Haut (FR)

(73) Assignee: Societe de Recherches et Techniques Dentaires-R.T.D., Saint Egreve (FR)

( * ) Notice: Subject to any disclaimer, the term of this patent is extended or adjusted under 35 U.S.C. 154(b) by 0 days.

(21) Appl. No.: 11/550,460

(22) Filed: Oct. 18, 2006

(65) Prior Publication Data

US 2008/0131847 A1  Jun. 5, 2008

(30) Foreign Application Priority Data

Oct. 18, 2005 (EP) .................... 05292190

(51) Int. Cl.
 *A61C 5/08* (2006.01)
(52) U.S. Cl. ........................ 433/220; 433/211
(58) Field of Classification Search .......... 433/215, 433/220–224
See application file for complete search history.

(56) References Cited

U.S. PATENT DOCUMENTS

| 4,850,874 | A | * | 7/1989 | Weissman | 433/225 |
|---|---|---|---|---|---|
| 5,326,263 | A | * | 7/1994 | Weissman | 433/224 |
| 5,342,200 | A | * | 8/1994 | Chalifoux | 433/220 |
| 5,989,032 | A | * | 11/1999 | Reynaud et al. | 433/224 |
| 6,183,253 | B1 | | 2/2001 | Billet et al. | 433/81 |
| 6,267,597 | B1 | | 7/2001 | Kim | 433/224 |
| 2002/0152929 | A1 | * | 10/2002 | Burgath et al. | 106/35 |
| 2003/0027102 | A1 | * | 2/2003 | Karmaker et al. | 433/220 |
| 2003/0148247 | A1 | * | 8/2003 | Sicurelli et al. | 433/220 |
| 2005/0123881 | A1 | * | 6/2005 | Karmaker et al. | 433/220 |

FOREIGN PATENT DOCUMENTS

| FR | 2 753 365 | | 3/1998 |
|---|---|---|---|
| GB | 2214087 | * | 8/1989 |
| WO | WO 01/08590 | | 2/2001 |

* cited by examiner

*Primary Examiner*—Ralph A Lewis
*Assistant Examiner*—Yogesh Patel
(74) *Attorney, Agent, or Firm*—Heslin Rothenberg Farley & Mesiti P.C.

(57) ABSTRACT

A dental post includes a composite material such as long fibers embedded in a resin matrix, and is able to transmit visible radiation when it is lit by a dental lamp to ensure polymerization of a product for setting in a tooth's root canal. The post, which has a specific color determined at ambient temperature before insertion into said canal, and which contains at least one thermochromic substance able to provide said specific color, loses its color when in place in the canal. A method for forming the dental post and a kit including a plurality of dental posts and drills are also disclosed.

15 Claims, 1 Drawing Sheet

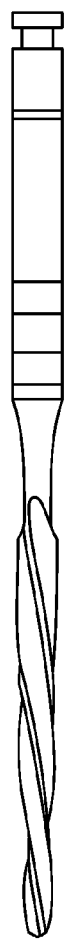
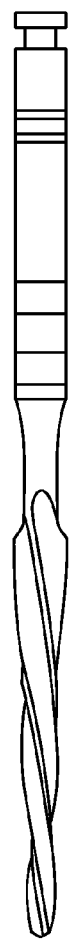
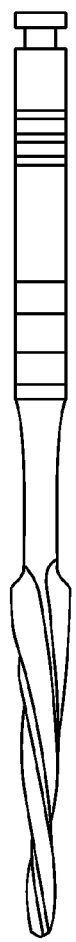
FIG. 1   FIG. 2   FIG. 3   FIG. 4

COLORED DENTAL POST

CROSS-REFERENCE TO RELATED APPLICATION

This application is a non-provisional U.S. filing based on European Patent Application EP05292190.5, filed Oct. 18, 2005, the priority of which is claimed herein and the entire disclosure of which is incorporated herein by reference.

FIELD OF THE INVENTION

This invention concerns a dental post and notably a post made of composite material which is capable, before being inserted into the root canal of a patient's tooth, of having a characteristic predetermined color notably of its diameter and, after insertion in said canal, of losing this color.

BACKGROUND ART

It is known in the dental art that the metal posts used for reconstituting pulpless teeth have been abandoned in recent years in favor of posts made of composite materials which provide many advantages and notably better resistance to phenomena of corrosion, and a transversal elasticity modulus similar to that of dentine providing them with better coherence therewith. While posts made of conventional composite materials are set in the root canal with cement, composite posts are made with transparent materials are also known which can transmit light, thus ensuring the polymerization of a setting adhesive as described in patent WO 01/08590.

It is known that the practitioner has various diameters of posts available to him as well as the corresponding drills. To ensure the fast, safe combination of each post/drill pair, it has been proposed that they be given a common color. Thus, the practitioner can establish this combination at a glance. If the color marking on the drill presents no particular technical difficulty, the same does not hold true for markings on the post. Various methods have been proposed for this, notably either by solid-dying the whole post, or applying a color to one end of it, or applying a ring or colored sleeve around the straight section.

While the various means proposed enable practitioners to easily recognize post diameters by their color, each of them has notable disadvantages.

Thus, the solid-dyed posts have the disadvantage of creating a colored sheen through the transparency when used with a ceramic prosthesis.

Applying paint to the tip of the post, on the other hand, stops the transmission of light directly to the inside of it, which requires the practitioner to cut said post before inserting it. Beyond the additional constraint required of the practitioner, this technique cannot be used with posts with a set, predetermined length.

Lastly, using a ring or a colored sleeve on each post is also a long, costly operation insofar as, to date, it has to be done by hand, post after post.

SUMMARY OF THE INVENTION

An aspect of the present invention is to offer a dental post which, when made available to the practitioner, has a determined color, preferably characteristic to its diameter, and which, nonetheless, when inserted into a tooth's root canal, loses its coloring, thus avoiding any coloring through the crown. Furthermore, this post can then recover its color under certain conditions to make it easier to locate it in case of another intervention.

Another aspect of the present invention is a dental post made of composite material comprising long fibers, preferably unidirectional and continuous, embedded in a resin matrix, said post being able to transmit visible radiation when it is lit by a dental lamp so as to ensure the polymerization of a substance for setting said post in the tooth's root canal, said post having a specific color determined before inserting it into said canal, characterized in that it contains at least one thermochromic substance capable of giving it said specific color when at ambient temperature and causing it to lose its color when placed in said canal.

BRIEF DESCRIPTION OF THE DRAWINGS

The subject matter which is regarded as the invention is particularly pointed out and distinctly claimed in the concluding portion of the specification. The invention, however, may best be understood by reference to the following detailed description of various embodiments and the accompanying drawings in which:

FIG. 1 is a side elevational view of a first sized dental drill having a black stripe and a corresponding dental post colored grey in accordance with the present invention;

FIG. 2 is a side elevational view of a second sized dental drill having two red stripes and a corresponding dental post colored pink in accordance with the present invention;

FIG. 3 is a side elevational view of a third sized dental drill having two yellow stripes and a corresponding dental post colored light yellow in accordance with the present invention;

FIG. 4 is a side elevational view of a fourth sized dental drill having two blue stripes and a corresponding dental post colored light blue in accordance with the present invention.

DETAILED DESCRIPTION

It is known that the thermochromic substances currently available in the market are made up of pigments which are in a colored state when they are found below a certain threshold temperature and lose this color as soon as they rise above this threshold temperature, becoming colored again when the temperature drops below said threshold temperature again. These pigments are preferably coated in micro-capsules, which makes them chemically stable in relation to their environment. Some of these pigments are sold in this form by the Kelly Chemical Corporation. Such pigments are available in different colors, characterized by normalized "pantone" references, and for different threshold temperatures.

The use of thermochromic substances in dental cements is known for setting inlays, crowns or bridges. Thus, patent application US 2002/0152929 describes such a sealing product which, at ambient temperature and at a temperature close to that of the patient's body, has an off-white tint which makes it invisible when covered by a ceramic crown and which, when cooled (or heated depending on the type of thermochromic substance used), takes on a characteristic color enabling the practitioner to detect any possible overflows of the substance around the tooth which could form during the sealing operation, in order to eliminate them, with the sealing product then taking on its initial tint when the thermal stimulus is halted.

In accordance with the invention, the quantity of thermochromic substance added to the resin matrix will be sufficient to give the post coloring that enables the practitioner to identify it by its color (and possibly to use it with the corresponding drill with the same color) and will be small enough to not darken it so that it will be able to transmit enough light during the usual lighting time by a polymerizing dental lamp so that a setting substance can be polymerized.

Preferably, in accordance with the present invention, the thermochromic substance content will be between 0.1 and 1% by weight of the resin matrix and/or 0.02 to 0.2% by weight of the post.

In one embodiment of the invention, the thermochromic substance will be such that the loss of color will occur at a threshold temperature between 30 and 40° C. and preferably at approximately 31° C.

The pigments used may advantageously be enclosed in micro-capsules which preserve them from direct contact with the resin matrix and whose envelope will be made of a substance that is biocompatible with the post's matrix, notably an acrylic resin.

In accordance with the invention, the resin matrix may contain at least one Bisphenol-A-based monomer; said monomer may be BisGMA resin based.

Beyond the fact that the present invention enables the practitioner to recognize the type of post by its color, it is also particularly interesting in case of re-treating a previously treated tooth. Indeed, when a pulpless tooth is reconstituted using a transparent post, it is particularly difficult for the practitioner who seeks to re-treat the tooth to recognize the exact position of the post due to its transparency. In accordance with the invention, it will be possible to make the post visible again by causing it to become colored again by cooling the upper part of the tooth using, for example, a cold fluid spray (air or water) applied to it. Given the reversible character of the thermochromic substance, the post loses its color again once the cooling stops.

The present invention also concerns a production method using pultrusion of a rod used to constitute, after machining, a dental post made of composite material comprising long fibers embedded in a resin matrix, said post containing furthermore at least one thermochromic substance enclosed in micro-capsules, characterized in that the temperature at which pultrusion is performed is lower than the micro-capsules' melting temperature. Preferably, the temperature at which pultrusion is performed will be below 200° C.

In accordance with the present invention, a dental post is produced by adding a given quantity of thermochromic pigments to the resin forming the composite post's matrix. More precisely, the dental post comprises a resin matrix, for example an epoxy resin matrix, or a methacrylic resin, with which a given quantity of thermochromic pigments is mixed and, conventionally, long, continuous unidirectional fibers made of a transparent material, notably fibers containing a radiopaque substance such as, for example, a metal oxide and notably zircon. The whole is produced following the technique known in the field of dental posts, that is in two essential steps, i.e. a first pultrusion step providing a rod and a second step of mechanical machining in which the post is given its shape and size.

The dental post in accordance with the present invention should present characteristics of transparency enabling it, once inserted into the tooth's root canal, to transmit visible radiation through said dental canal and to distribute said radiation to the periphery of the post in order to ensure the polymerization of a sealing product spread between the dental post and its housing. Such a dental post must therefore have light transmitting or transparency characteristics sufficient for the polymerization operation to be performed successfully.

The dental post in accordance with the invention, furthermore, must, when outside the tooth, and therefore when subjected to ambient temperature, i.e. below the threshold temperature, present sufficient coloring for its color to be easily recognizable by the practitioner. It will thus be possible to provide the post with a given color depending on the diameter of the post and which will correspond to the color of the drill used by the practitioner to work the tooth's root canal to the desired diameter.

The color associated with the post will be obtained with its intrinsic solid color, and not, for example, by adding painted marks or applying an additional colored ring, thus avoiding costly handling and risks of error.

In accordance with the invention, care will be taken that the quantity of thermochromic pigments added to the resin matrix does not affect the mechanical qualities of the post on the one hand and, on the other, does not impede the transmission of the quantity of light necessary for the polymerization of its setting product.

Table I below represents a certain number of parameters for dental posts in accordance with the invention. Thus, the columns of the table below successively represent the reference for the color used, the proportion of pigments in a Biphenol A resin matrix, the value of the post's interlaminar shear strength and flexural strength, respectively, and lastly the transmission of light at the start and end of polymerization, respectively, said measurements having been made at an ambient temperature of approximately 25° C., thus below the threshold temperature.

TABLE I

| Pigment Pantone reference | Proportion of pigments in the resin (by weight) | Interlaminar shear strength | Flexural strength | Transmission of light in mm-start of polymerization-complete polymerization |
|---|---|---|---|---|
| Colorless (ref. JTO) | Not applicable | 65 MPa | 1600 MPa | 45 mm 40 mm |
| Yellow YT-31 Pantone 108C | 0.6% | 67 MPa | 1640 MPa | 20 mm 17.5 mm |
| Red RT-31 Pantone 186C | 0.6% | 64 MPa | 1620 MPa | 20 mm 17.5 mm |
| Blue BT-31 Pantone 301U | 0.3% | 67 MPa | 1660 MPa | 17.5 mm 15 mm |
| Green DT-31 Pantone 335C | 0.4% | 66 MPa | 1630 MPa | 20 mm 17.5 mm |
| Black LT-31 Pantone 5C2X | 0.4% | 63 MPa | 1646 MPa | 20 mm 17.5 mm |
| Orange OT-31 Pantone 021C | 0.2% | 62 MPa | 1593 MPa | 30 mm 25 mm |
| Purple VT-31 Pantone 278C | 0.4% | 62 MPa | 1648 MPa | 25 mm 20 mm |

The values given in this table were obtained from tests performed on composite material rods with a diameter of 2.50 mm, rods which are then machined to make the posts. The mechanical characteristics for shear and flexural strength were obtained following the ISO 14130 and 14125 standards, respectively. The distance between supports was 12.5 mm for interlaminar shear tests and 50 mm for flexural tests.

The value mentioned concerning the transmission of light corresponds to a maximum sample length, permitting complete polymerization of a drop of light-curing resin for setting the post in the tooth's root canal, of the brands "Sealbond Bonding Resin" or "Dentin Enamel Resin" manufactured by the Bisco corporation.

The protocol applied to measure light transmission was the following:
a) a 50-mm long sample was taken,
b) this sample was graduated every 5 mm and inserted into a black plastic plate, 1 mm thick, which does not let light through,
c) a drop of light-curing resin of the type mentioned above is deposited on the bottom end of the sample,
d) the top end of the sample is exposed to the rays from a curing lamp providing 400 W/cm² for 40 seconds,
e) when the resin was not completely polymerized under these lighting conditions, the length of the sample was reduced by 5 mm, and
f) the three previous operations were repeated until complete polymerization of the drop of resin was achieved.

Under these conditions, light transmission corresponds to the maximum length of the sample providing complete polymerization of said drop of resin.

If we compare the results for the post in accordance with the invention with the characteristics of an otherwise identical post, but to which no thermochromic substance has been added (cf. 1st line of the table), we can see that the interlaminar shear strength characteristic is almost integrally preserved whatever the thermochromic pigment used, and the same holds true for the flexural strength characteristic.

Concerning the transmission of light characteristic, we can see that it decreases significantly, but we can see that it nonetheless achieves total polymerization in a post with a length of 16 mm, which basically corresponds to the maximum length of the posts used in dental techniques.

We could, of course, combine several thermochromic pigments with different colors to obtain a new color or a new shade of color.

TABLE II

| Pigment Pantone reference | Proportion of pigments in the resin (by weight) | Interlaminar shear strength | Flexural strength | Transmission of light in mm-start of polymerization-complete polymerization |
|---|---|---|---|---|
| Green: mixture of BT-31 blue and YT-31 yellow | Blue 0.05% Yellow 0.25% | 71 MPa | 1596 MPa | 25 mm 17.5 mm |

Thus, as represented in Table II above, blue and yellow pigments are mixed into the resin matrix used to produce the post which, once the post is finished, will give the post a green color whose interlaminar shear strength and flexural characteristics are fully preserved and whose transmission characteristic is 17.5 mm.

It is understood that the greater the post's thermochromic substance content, the more the post's color is saturated at ambient temperature, which will make it easier to identify when chosen by the practitioner before insertion into the root canal and, secondly, to locate when re-treating by cooling the tooth, but the light transmission will not be as good once the post is in place. It has been established that a thermochromic substance content between 0.02 and 0.2% by weight of the post or between 0.1 and 1% by weight of the resin matrix provides sufficient light transmission to ensure polymerization of the setting product with full safety while enabling the post to keep enough color at ambient temperature to be identified easily.

The invention also concerns a kit containing posts as previously disclosed, each post having a specific color characteristic of the diameter of said post. In a preferred embodiment, the kit, e.g., as shown in FIGS. 1-4, also contains corresponding drills, i.e. drills having a diameter identified by a color identical to the posts having the same diameter. Practically, the kit contains 4 to 5 different diameters of posts, said diameter being comprised between 0.8 and 2.3 mm. Drills can be identified by several means as for example rings or stripes.

The invention claimed is:

1. A plurality of single-piece dental posts comprising:
   each of said plurality of single-piece dental posts comprising a composite material comprising unidirectional and continuous long fibers embedded in a resin matrix containing at least one thermochromic substance, said composite material defining said single-piece post having a generally cylindrical upper portion and a generally tapering lower portion,
   each of said plurality of single-piece dental posts comprising a different diameter characteristic,
   each of said plurality of single-piece dental posts comprising a quantity of the at least one thermochromic substance added to the resin matrix that is sufficient to give each of said plurality of dental posts a specific different color at ambient temperature and which specific different colors correspond to one of said different diameter characteristics of said plurality of dental posts, and so that each of said dental post loses the specific different color when said dental post is inserted into a tooth's root canal, and
   wherein each of said plurality of dental posts comprising said long fibers, said at least one thermochromic substance, and said resin matrix being sufficiently transparent so that after insertion of said post into the tooth's root canal said post allows transmission of visible radiation through said post when lit with a dental lamp to ensure the polymerization of a product to permit setting of said post in the tooth's root canal.

2. The dental post of claim 1 wherein the thermochromic substance content is between 0.02 and 0.2% by weight of the post.

3. The dental post of claim 1 wherein the thermochromic substance content is between 0.1 and 1% by weight of the resin matrix.

4. The dental post of claim 1 wherein the thermochromic substance is such that the specific color loss of the dental post occurs at a threshold temperature between 30 and 40° C.

5. The dental post of claim 4 wherein the thermochromic substance is such that said threshold temperature is approximately 31° C.

6. The dental post of claim 1 wherein the thermochromic substances are enclosed in micro-capsules.

7. The dental post of claim 6 wherein the envelopes of the micro-capsules are made of an acrylic resin.

8. The dental post of claim 1 wherein the resin matrix contains at least one Bisphenol-A-based monomer.

9. The dental post of claim 8 wherein said monomer is BisGMA resin based.

10. The dental post of claim 1 wherein said post contains radiopaque fibers.

11. The dental post of claim 10 wherein the radiopaque fibers contain a metal oxide, and notably zircon.

12. A kit comprising:
A plurality of dental posts of claim 1, and
wherein each of the plurality of posts having a specific color characteristic of a diameter of said post.

13. The kit of claim 12 wherein the diameters of said plurality of posts comprise a diameter between 0.8 and 2.3 mm.

14. The kit of claim 12 containing 4 different diameters of posts.

15. The kit of claim 12 further comprising a plurality of drills having diameters identified by a color corresponding to the posts having the same diameter.

* * * * *